(12) United States Patent
Magara

(10) Patent No.: US 7,148,880 B2
(45) Date of Patent: Dec. 12, 2006

(54) INPUT OPERATING DEVICE FOR ACCEPTING A PLURALITY OF INPUT OPERATIONS BY ONE OPERATING MEMBER

(75) Inventor: Yutaka Magara, Tokyo (JP)

(73) Assignee: Nemoto Kyorindo Co., Ltd., Tokyo (JP)

(*) Notice: Subject to any disclaimer, the term of this patent is extended or adjusted under 35 U.S.C. 154(b) by 376 days.

(21) Appl. No.: 10/476,179

(22) PCT Filed: Sep. 13, 2002

(86) PCT No.: PCT/JP02/09449

§ 371 (c)(1),
(2), (4) Date: Nov. 5, 2003

(87) PCT Pub. No.: WO03/025733

PCT Pub. Date: Mar. 27, 2003

(65) Prior Publication Data

US 2004/0130529 A1 Jul. 8, 2004

(30) Foreign Application Priority Data

Sep. 14, 2001 (JP) ............................. 2001-279889

(51) Int. Cl.
*G09G 5/08* (2006.01)
*H01H 25/04* (2006.01)
*G05G 9/047* (2006.01)

(52) U.S. Cl. .................. 345/161; 200/5 R; 74/471 XY (58) Field of Classification Search ................ 345/161, 345/156; 200/5 R, 6 A; 273/148 B; 74/471 XY
See application file for complete search history.

(56) References Cited

U.S. PATENT DOCUMENTS

2002/0196232 A1* 12/2002 Chen .......................... 345/161

FOREIGN PATENT DOCUMENTS

| JP | 63-262519 | | 10/1988 |
|----|-----------|---|---------|
| JP | 5-113849 | | 5/1993 |
| JP | 5-232917 | | 9/1993 |
| JP | 05232917 A | * | 9/1993 |
| JP | 5-282374 | | 10/1993 |
| JP | 6-190145 | | 7/1994 |
| JP | 7-168690 | | 7/1995 |
| JP | 8-294485 | | 11/1996 |
| JP | 08294485 A | * | 11/1996 |
| JP | 10-214128 | | 8/1998 |
| JP | 10214128 A | * | 8/1998 |
| JP | 2001-29658 | | 2/2001 |

* cited by examiner

*Primary Examiner*—Amr A. Awad
*Assistant Examiner*—Stephen G Sherman
(74) *Attorney, Agent, or Firm*—Oblon, Spivak, McClelland, Maier & Neustadt, P.C.

(57) ABSTRACT

In the present invention, a freely rotatable rotating part in which a single multidirectional switch is mounted is assisted to an initial position by a rotation recovery means, and the rotation from this initial position is detected by a rotation detection means. As a result, inclination of a control part toward the front or rear or toward the right or left or rotation of the control part toward the right or left can each be individually detected, and when this inclination or rotation of the control part is suspended, the control part can be automatically returned to the initial position. Accordingly, an input control device, in which a control part that has been inclined toward the front or rear or toward the right or left or rotated to the right or left automatically returns to its initial position, can be realized by a simple construction.

6 Claims, 12 Drawing Sheets

| | -45° | -30° | -15° | 0° | +15° | +30° | +45° |
|---|---|---|---|---|---|---|---|
| sensor ① | × | ○ | ○ | × | × | ○ | ○ |
| sensor ② | ○ | × | ○ | × | ○ | × | ○ |
| sensor ③ | ○ | ○ | ○ | × | × | × | × | left ⟵⟶ right

INPUT OPERATING DEVICE FOR ACCEPTING A PLURALITY OF INPUT OPERATIONS BY ONE OPERATING MEMBER

TECHNICAL FIELD

The present invention relates to an input control device for accepting a plurality of input operations at a single control part, and more particularly to an input control device in which a control part can be inclined in the X-axis and Y-axis directions and rotated around the Z-axis.

BACKGROUND ART

Figure 1:
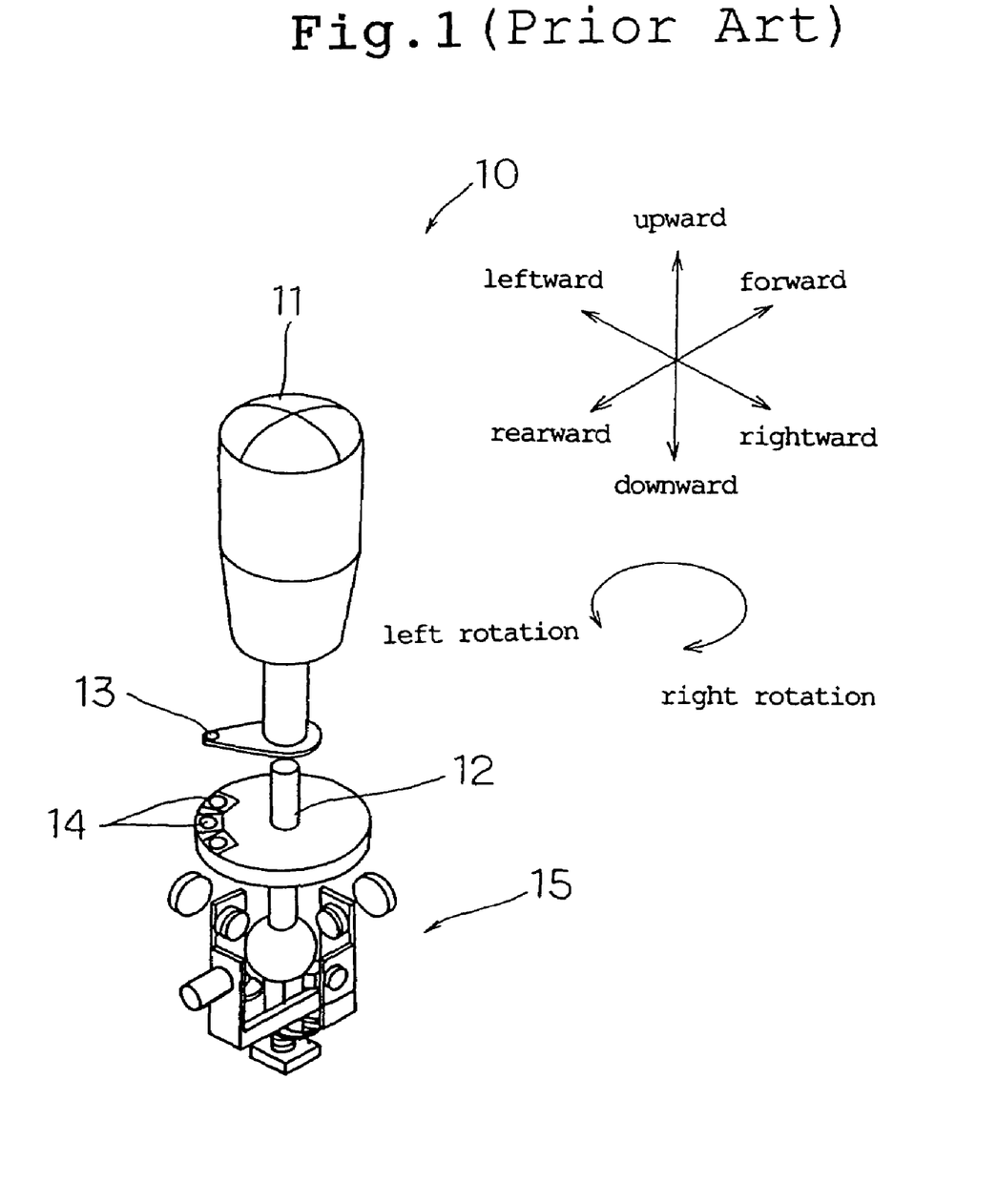
FIG. 1 is a perspective view showing a prior-art example of an input control device.

Various types of input control devices are currently in use, and some of these types accept a plurality of types of input operations at a single control part. As one example of such an input control device of the prior art, FIG. 1 shows the input control device that is disclosed in Japanese Patent Laid-Open No. H10-214128.

As the control part, this input control device 10 includes stick-shaped control part 11 that is long and narrow in the vertical direction, i.e., the Z-axis direction. This control part 11 is supported by an axial support structure that is made up by support axis 12 that allows free rotation to the left and right, and moreover, that is freely displaceable in the vertical direction.

One contact point 13 that extends toward the outside is formed on the lower end of control part 11, and three contact points 14 that are selectively conductive with this contact point 13 are mounted on support axis 12, thereby forming a rotation detection means for detecting the rotation of control part 11. In addition, a Z-axis detection means for detecting downward displacement of control part 11 is formed by, for example, a pressure-sensitive sensor (not shown in the figure).

Support axis 12 is supported by support mechanism 15 having a dual construction that allows free inclination to the left and right, which is the X-axis direction, as well as inclination to the front and rear, which is the Y-axis direction. An X-axis detection means for detecting inclination to the right and left and a Y-axis detection means for detecting inclination in the forward and rearward directions are formed by, for example, pressure-sensitive sensors (not shown in the figure).

In input control device 10 of the above-described construction, control part 11 is capable of inclination forward and rearward and inclination to the left and right, rotation to the left and to the right, and downward displacement; and a plurality of types of input operations can therefore be executed at one time by means of one control part 11.

Computed Tomography (CT) scanners or Magnetic Resonance Imaging (MRI) devices are currently being used in medical facilities as an image pick-up means for capturing image data of a plurality of sequence coaxial tomographs from a human body, and various types of image display devices have been developed to display the image data of these devices.

Such an image display device can be realized by, for example, installing specialized application software in a personal computer, and then displaying on an image display device a plurality of sequence image data in order that have been stored as sequence data. In a typical personal computer, however, input operations are executed by means of a mouse or a keyboard on which input keys such as alphabet keys are arranged, and although such an input means has the advantage of wide applicability, it has the disadvantage of poor controllability.

An image display device for which the current applicant submitted an application as Japanese Patent Application No. 2001-038522 includes a specialized input control device, and this input control device includes a control part that can freely slide in the rearward and forward directions. In this image display device, sliding the control part backward and forward causes successive switching of the image data that are displayed on the display in accordance with this operation, whereby a plurality of sequence tomographic image data can be easily viewed.

In the interest of further improving the controllability of the above-described image display device, the present applicant next originated a construction in which the input control device is a construction such as the previously described input control device 10 and submitted an application as Japanese Patent Application No. 2001-105754. In previously described input control device 10, input is possible at single control part 11 not only by inclination in the rearward and forward directions but also by inclination to the right and left, rotation, and vertical displacement, and a further improvement in the controllability of the image display device can therefore be expected.

However, input control device 10 that was disclosed in the previously described Japanese Patent Laid-Open No. H10-214128 was of a construction in which, when control part 11 was inclined backward and forward, inclined to the right and left, or rotated to the right and left, control part 11 remained at that position.

In other words, when control part 11 was manually operated and an operation signal generated, control part 11 had to be manually returned to the initial position in order to cancel the operation signal. Although this form of operation is effective for the device to which it was applied, this form is not suitable for an image display device that successively displays a plurality of sequence image data.

In addition, although the direction of inclination is inscribed on the upper surface of control part 11 in previously described input control device 10, these inscribed directions and the direction of inclination do not agree when control part 11 is rotated, and this introduces potential for error. Further, although inexpensive multidirectional switches are currently marketed as package components that can be mounted on a circuit substrate, support mechanism 15 for inclining control part 11 forward and rearward and to the right and left is formed as a special construction in the previously described input control device 10, and the use of marketed multidirectional switches is therefore problematic.

Finally, in previously described input control device 10, rotation of control part 11 is detected in three steps by means of three ON/OFF switches made up by three contact points 14. If the middle contact point 14 is taken as the initial position, rotation toward the left and right can be detected in only one step for each direction. Adding contact points 14 can be considered as a means of increasing the detection steps, but this approach would also result in an increase in the number of components and a decrease in productivity.

DISCLOSURE OF INVENTION

The present invention was developed in consideration of the above-described problems, and therefore has as objects: the provision of an input control device in which a control part that inclines in the XY directions and rotates around the Z-axis automatically returns to its initial position; and further, the provision of an image display device for displaying image data in accordance with the input operations of this input control device.

The input control device of the present invention includes: a control part, a support mechanism, a inclination recovery means, an X-axis detection means, a Y-axis detection means, a rotating part, an axial support mechanism, a rotation recovery means, and a rotation detection means; wherein this control part accepts input. This control part is supported by the support mechanism such that the control part can freely incline in the X-axis direction and in the Y-axis direction, and this control part is further assisted by the inclination recovery means to the initial position of inclination in the X-axis direction and Y-axis direction. Inclination of the thus-assisted control part in the X-axis direction from the initial position is detected by the X-axis inclination detection means, and inclination in the Y-axis direction is detected by the Y-axis inclination detection means, whereby inclination in the X-axis direction and Y-axis direction of the control part is detected for each direction of inclination. The above-described support mechanism, inclination recovery means, X-axis detection means, and Y-axis detection means are all mounted as a single unit on the rotating part; and this rotating part is in turn supported by the axial support mechanism rotatably around the Z-axis, whereby the control part, when inclined in X-axis direction and Y-axis direction, rotates around the Z-axis. This axially supported rotating part is assisted by a rotation recovery means to return to the initial position of rotation, and rotation of this assisted rotating part around the Z-axis from the initial position is detected by the rotation detection means, whereby rotation of the control part around the Z-axis is detected.

In the input control device of the present invention, when the control part is inclined in the X-axis direction or Y-axis direction or rotated around the Z-axis, the control part is assisted back to the initial position, and as a result, the control part can return to the initial position automatically when inclination or rotation of the control part is canceled, and cancellation of an input operation can automatically halt the generation of a control signal.

As another aspect of the above-described input control device, a single multidirectional switch includes: the control part; the support mechanism, the inclination recovery means, the X-axis detection means, and the Y-axis detection means; and this small-scale first circuit substrate on which this multidirectional switch is mounted is in turn installed on a rotating part; and as a result, the means for detecting inclination in the X-axis direction and Y-axis direction is realized by marketed components that are mounted on the circuit substrate, and this means is mounted on the rotating part. This rotating part is axially supported on a base part rotatably by an axial support mechanism, and a sensor element that serves as a rotation detection means is mounted on a large-scale second circuit substrate that is installed on this base part, whereby a means for detecting rotation around the Z-axis is realized by marketed components that are mounted on a circuit substrate.

In the above-described input control device, a small-scale first circuit substrate, on which a single multidirectional switch is mounted, is installed on a rotating part; and sensor elements that serve as a rotation detection means are mounted on a large-scale second circuit substrate, and as a result, inclination in the X-axis direction and Y-axis direction as well as rotation around the Z-axis can be detected by marketed components that are mounted on a circuit substrate, and a mechanism that enables inclination can be made freely rotatable by means of a simple construction.

As another aspect of the above-described input control device, a plurality of sensor elements for detecting the rotation of the rotating part in the forward and reverse directions in a plurality of steps is mounted on the second circuit substrate, whereby the rotation of the control part around the Z-axis is detected in a plurality of steps according to angle of rotation. Accordingly, the rotation of the rotating part is detected by a plurality of sensor elements in the forward and reverse directions and in a plurality of steps, whereby the rotation of the control part around the Z-axis can be detected in a plurality of steps of rotation angles.

The image display device of the present invention includes: the input control device of the present invention, an image storage means, an image display means, and an image switching means; and stores at least one sequence data that is made up from a plurality of sequence image data in the image storage means. At least one frame of image data from these stored sequence data is displayed on the image display means, and this displayed frame of image data is sequentially switched in the forward or reverse direction by the image switching means in accordance with rotation of the control part in the forward and reverse directions around the Z-axis in the input control device. As a result, rotation in the input control device causes a plurality of frames of image data of the sequence data to be rapidly displayed in order, and the advance or reverse of this display switching is also controlled by the rotation in the forward or reverse direction of the input control device. A plurality of frames of image data of the sequence data can thus be rapidly viewed in order by means of simple input control, and the advance or reverse of this display switching can also be easily controlled.

As another aspect of the image display device of the present invention, the image data that are displayed on the image display means are switched one frame at a time in the forward or reverse direction by the image switching means each time the control part of the input control device is inclined in the forward or reverse direction of the Y-axis, whereby a plurality of frames of image data of the sequence data are displayed in order one frame at a time by inclination in the input control device, and the advance or reverse of this display switching is controlled by inclination in the forward or rearward direction in the input control device. Accordingly, a plurality of frames of image data of sequence data can be viewed in order one frame at a time by a simple input operation, and the advance or reverse of this display switching can also be easily controlled.

As another aspect of the image display device of the present invention, a plurality of frames of image data that are displayed in parallel by an image display means are switched at the same speed while remaining in synchronization by an image switching means, whereby a plurality of frames of image data that are displayed in parallel are similarly switched to enable comparison and investigation of a plurality of sequence data frame by frame of the image data.

As another aspect of the image display device of the present invention, the object of processing of the image switching means is selected from a plurality of frames of image data that are displayed in parallel by the image display means by means of an image selection means in accordance with inclination in the X-axis direction of the control part of the input control device, whereby the plurality of frames of image data that are displayed in parallel are selected by the input operations to the input control device and one desired frame from a plurality of frames of image data that are displayed in parallel can be selected and display-switched by a simple input operation.

As another aspect of the image display device of the present invention, image data that are displayed on an image display means are switched by an image switching means at a speed that accords with the angle of rotation of the control part of the input control device, whereby the speed of switching a plurality of frames of image data that are rapidly displayed in order is controlled by the angle of rotation in the input control device, and the speed of switching a plurality of frames of image data that are rapidly displayed in order can be controlled by a simple input operation.

Each of the various means described in the present invention may take any form to realize its function, and for example, may be dedicated hardware that exhibits a prescribed function, may be an image display device that is provided with prescribed functions by a computer program, may be prescribed functions that are realized in an image display device by a computer program, or may be a combination of these forms. In addition, each of the various means described in the present invention need not exist independently, but one means may be a portion of another means, or a portion of one means and a portion of another means may coincide.

Further, the image display device described in the present invention may be hardware that is capable of reading a computer program and executing corresponding processing operations; and for example, may be hardware that includes a CPU (Central Processing Unit) as the main unit to which are connected various devices such as ROM (Read Only Memory), RAM (Random Access Memory), and an I/F (Interface) unit.

In the present invention, the execution of various operations on an image display device in accordance with a computer program also permits the operation and control of various devices by the image display device. For example, the saving of various types of data in an image display device may be realized by storing various data in an information storage medium such as RAM that is included as a portion of the image display device, or by storing various data in an information storage medium such as a FD (Floppy Disk) that is loaded exchangeably in the image display device.

BEST MODE FOR CARRYING OUT THE INVENTION

We next describe an embodiment of the present invention with reference to the accompanying drawings.

Figure 2:
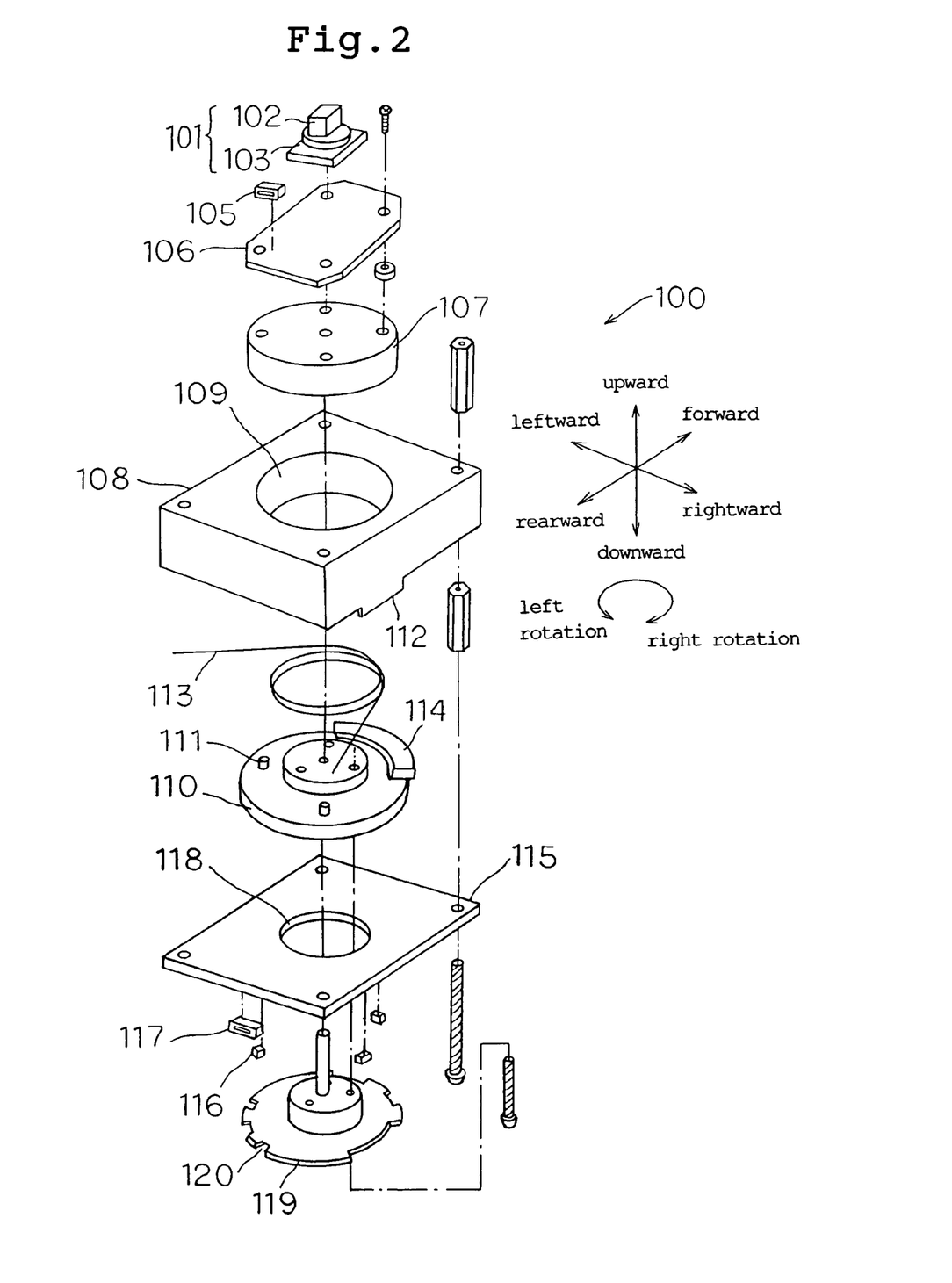
FIG. 2 is an exploded perspective view showing an embodiment of an input control device of the present invention.
Figure 3:
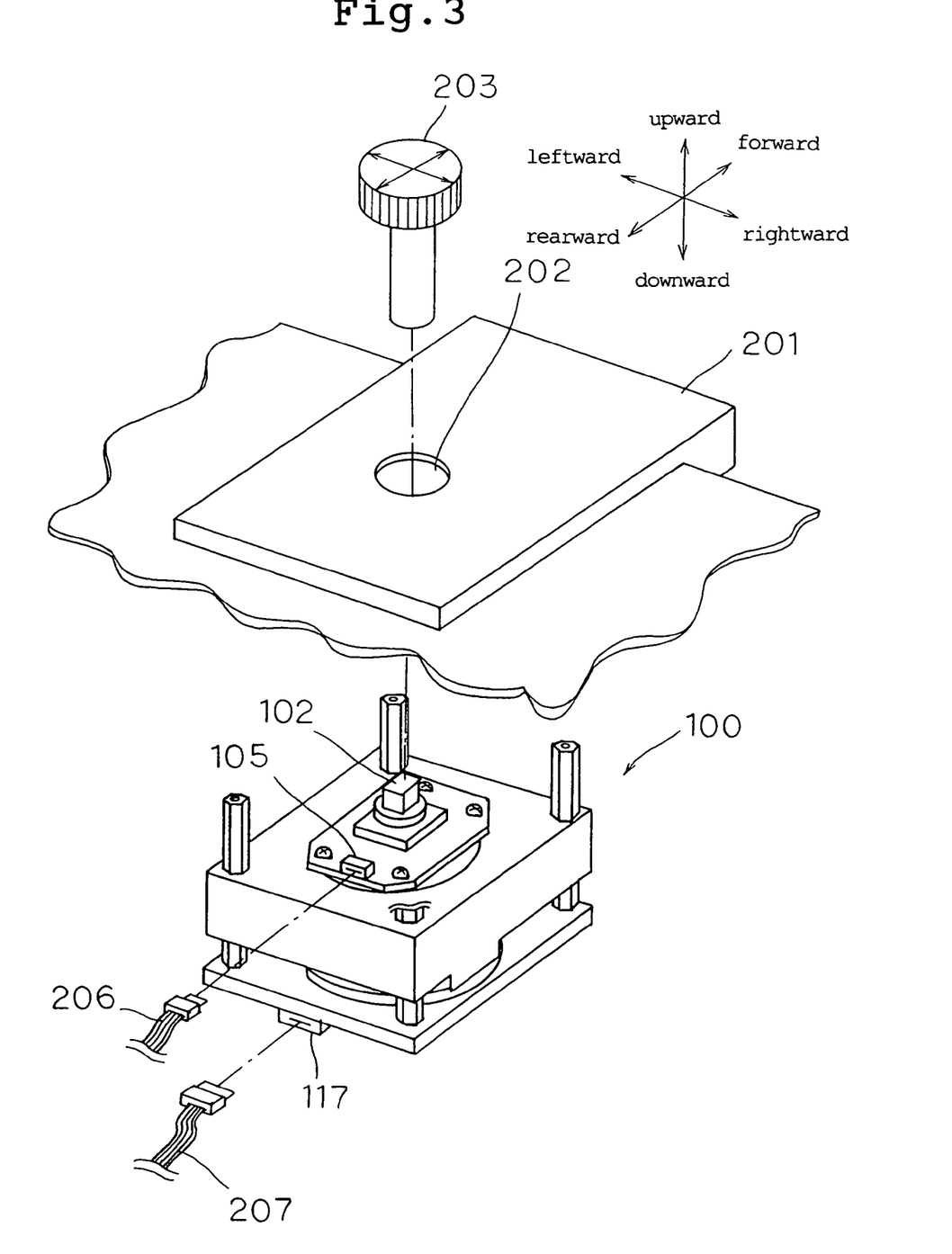
FIG. 3 is an exploded perspective view of the principal parts of a control unit.

As shown in FIG. 2 and FIG. 3, input control device 100 of the present embodiment includes: one four-directional switch 101, which is a multidirectional switch that is marketed as a package product; and this four-directional switch 101 includes control part 102 and main switch unit 103.

This four-directional switch 101 incorporates a support mechanism (not shown in the figures) in main switch unit 103, whereby control part 102 is supported such that free inclination is allowed in the right and left directions, i.e., the X-axis direction, and in the forward and rearward directions, i.e., the Y-axis direction. In addition, an inclination recovery means (not shown in the figures) is also incorporated, and this inclination recovery means elastically assists control part 102 to its central initial position. Further, an X-axis detection means and a Y-axis detection means are also incorporated (not shown in the figures), whereby the forward and rearward inclination as well as inclination to the right and left of control part 102 are each detected.

Four-directional switch 101 also incorporates a displacement mechanism (not shown in the figures) in main switch unit 103, whereby control part 102 is supported so as to allow free displacement in the vertical direction, i.e., the Z-axis direction. In addition, four-directional switch 101 also incorporates a displacement recovery means (not shown in the figure), and this displacement recovery means elastically assists control part 102 to its upper initial position. Four-directional switch 101 further incorporates a Z-axis detection means (not shown in the figure), whereby downward displacement of control part 102 is detected.

This four-directional switch 101 is mounted on small-scale first circuit substrate 106 together with connector 105, and four-directional switch 101 and connector 105 are linked by the printed wiring of this first circuit substrate 106. First circuit substrate 106 is secured to the upper surface of cylindrical resin rotating part 107, and this rotating part 107 is fits into round hole 109 of resin base part 108 which serves as the axial support mechanism such that rotating part 107 is rotatable to the left and right.

Rotating part 107 passes through this round hole 109 of base part 108; assistant part 110 having a disk shape and two-stepped form is secured to the bottom surface of rotating part 107; and linking protrusions 111 and 112 are formed on the top surface of this assistant part 110 and on the bottom surface of base part 108, respectively. Coil spring 113, which forms the rotation recovery means, is installed in assistant part 110 so as to link with linking protrusion 111, and the two ends of this coil spring 113 that protrude from this assistant part 110 also link with linking protrusion 112 of base part 108, whereby rotating part 107 is elastically assisted to initial position of rotation.

In addition, linking protrusion 114 having an arc shape is formed on the front upper portion of assistant part 110, and the connection of this linking protrusion 114 with linking protrusion 112 of base part 108 and limits the angle of rotation of rotating part 107 to 45° to both the left and right from the initial position.

A large second circuit substrate 115 that is secured to base part 108 is located below assistant part 110; and three sensor elements 116, which serve as the rotation detection means, are mounted together with connector 117 on the lower surface of this second circuit substrate 115. Sensor elements 116 are composed of reflective photocouplers, which are marketed package components, and these sensor elements 116 are connected to connector 117 by the printed wiring of second circuit substrate 115.

A round hole 118 is also formed in this second circuit substrate 115, and an upper circular portion of detection part 119 that passes through this round hole 118 is secured to rotating part 107. The lower portion of this detection part 119 is formed in a disc shape, and as shown in FIG. 2 and FIG. 4, notches 120 of different shapes are formed at positions that confront three sensor elements 116.

Three sensor elements 116 outputs binary signals indicating the detection of detection part 119, and these binary signals therefore produce $2^3=8$ combinations. Notches 120 are formed such that the combinations of the detection results of three sensor elements $116_1$–$116_3$ change with every 15° of rotation of detection part 119 to the left and right from the initial position.

Figure 4:
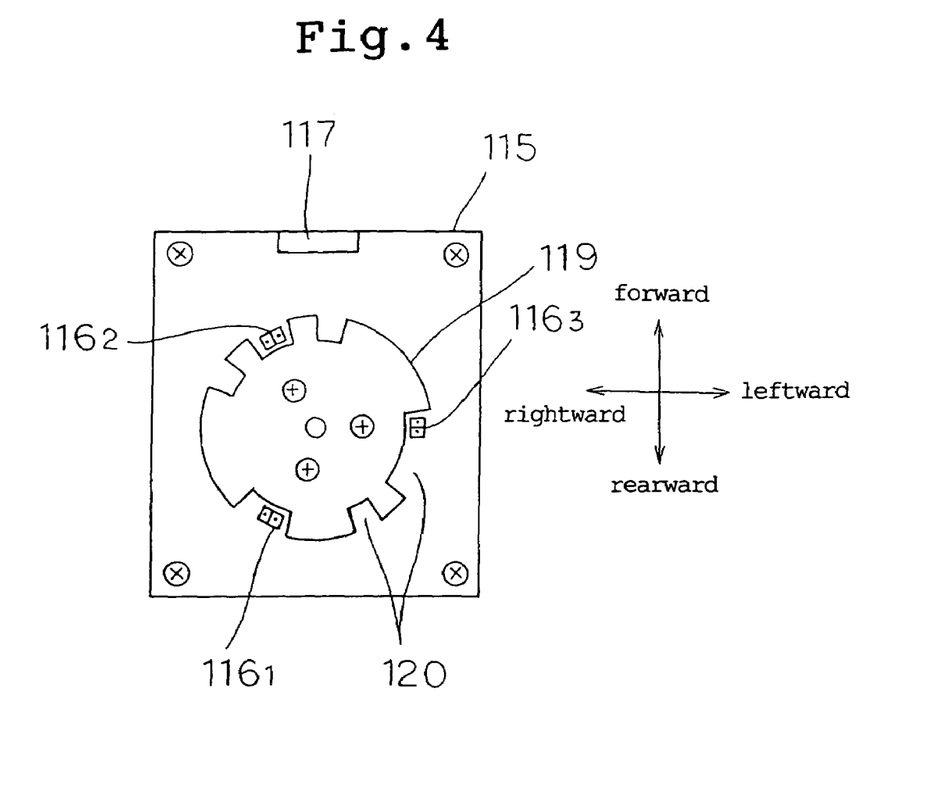
FIG. 4 is a bottom view showing the construction of a portion of a sensor element and a detection part of an input control device.
Figure 5:
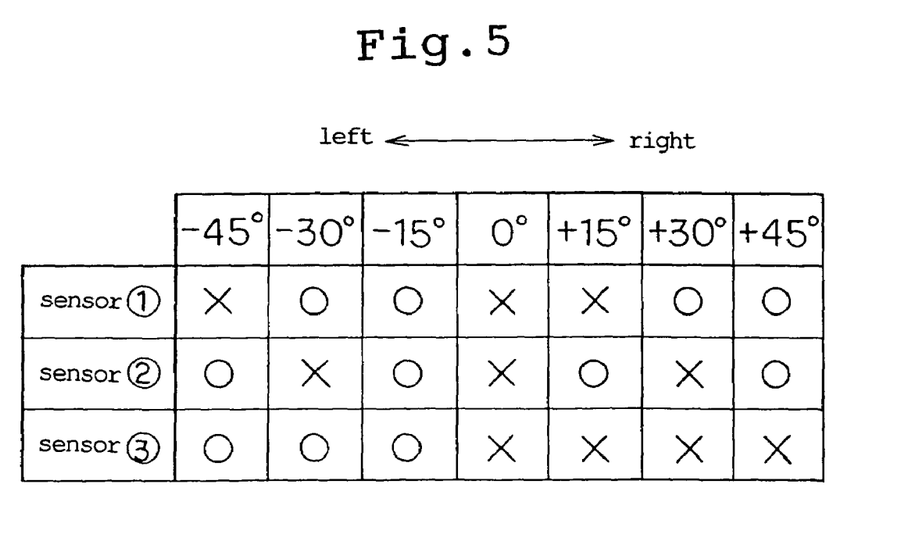
FIG. 5 is a schematic view showing the relation between the rotational angle of a detection part and the output signals of the sensor elements.

Thus, as shown in FIG. 4 and FIG. 5, when detection part 119 is arranged at the initial position, the rotated position of detection part 119 is detected in three steps every 15° to 45° to the left and right from the initial position by means of the combinations of the three output signals of sensor elements $116_1$–$116_3$.

Figure 6:
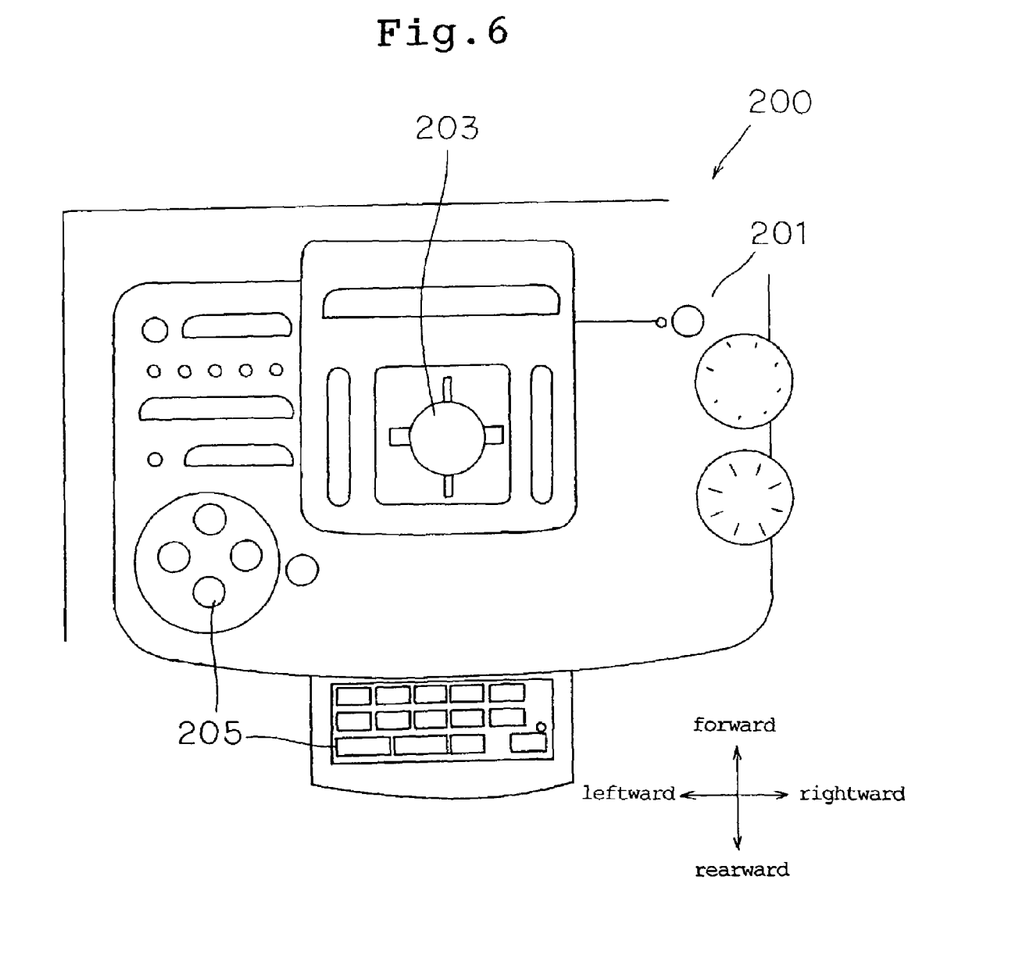
FIG. 6 is a plan view showing the outer appearance of a control unit.

As shown in FIG. 3 and FIG. 6, input control device 100 of this embodiment is incorporated in main housing 201 of control unit 200, and joystick 203 that passes through round hole 202 of this main housing 201 is attached as a single unit to control part 102 of input control device 100.

Control unit 200 is provided with various types of control keys 205, and also incorporates a circuit substrate (not shown in the figure) that is wired to these control keys 205. Parallel cables 206 and 207 are also wired to this circuit substrate, and these parallel cables 206 and 207 are connected removable to connectors 105 and 117 of input control device 100.

Figure 7:
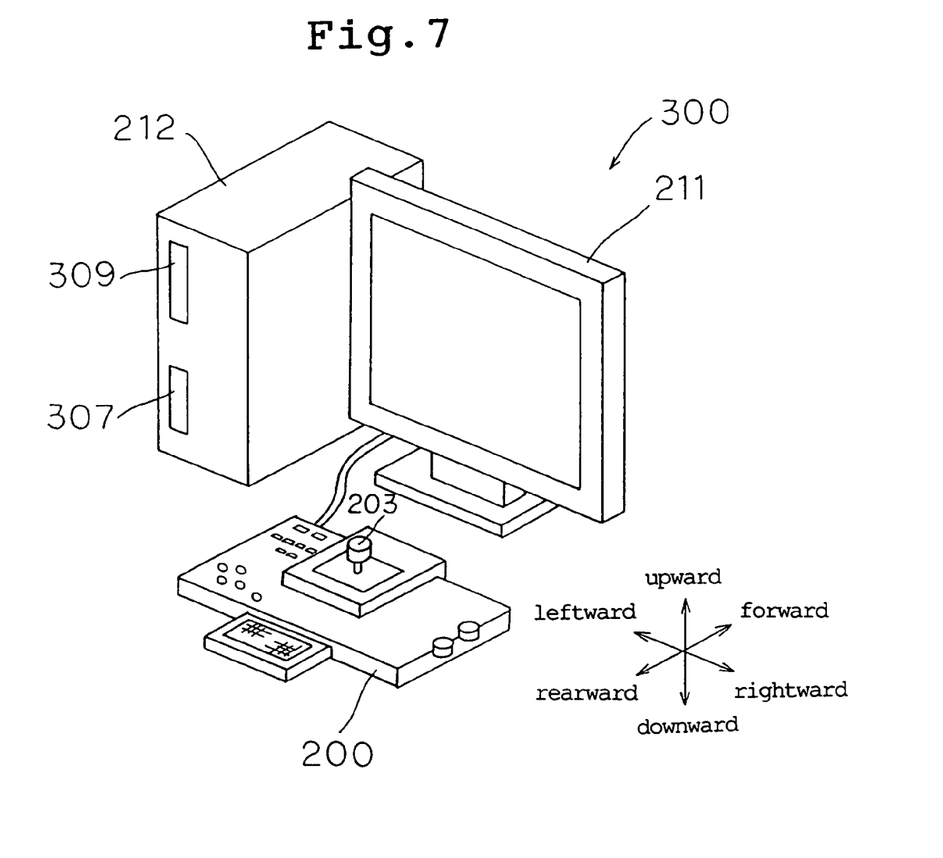
FIG. 7 is a perspective view showing the outer appearance of an image display device.
Figure 8:
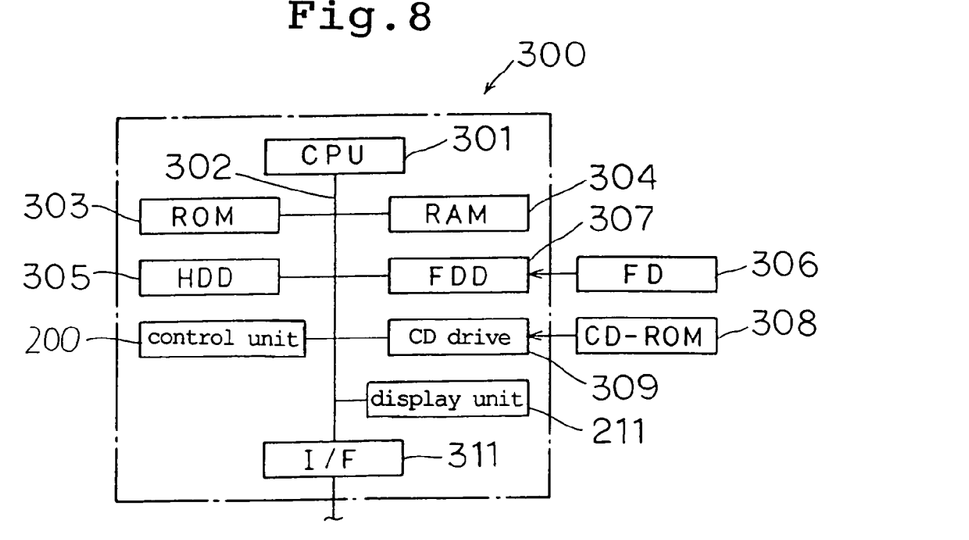
FIG. 8 is a block diagram showing the physical structure of an image display device.
Figure 9:
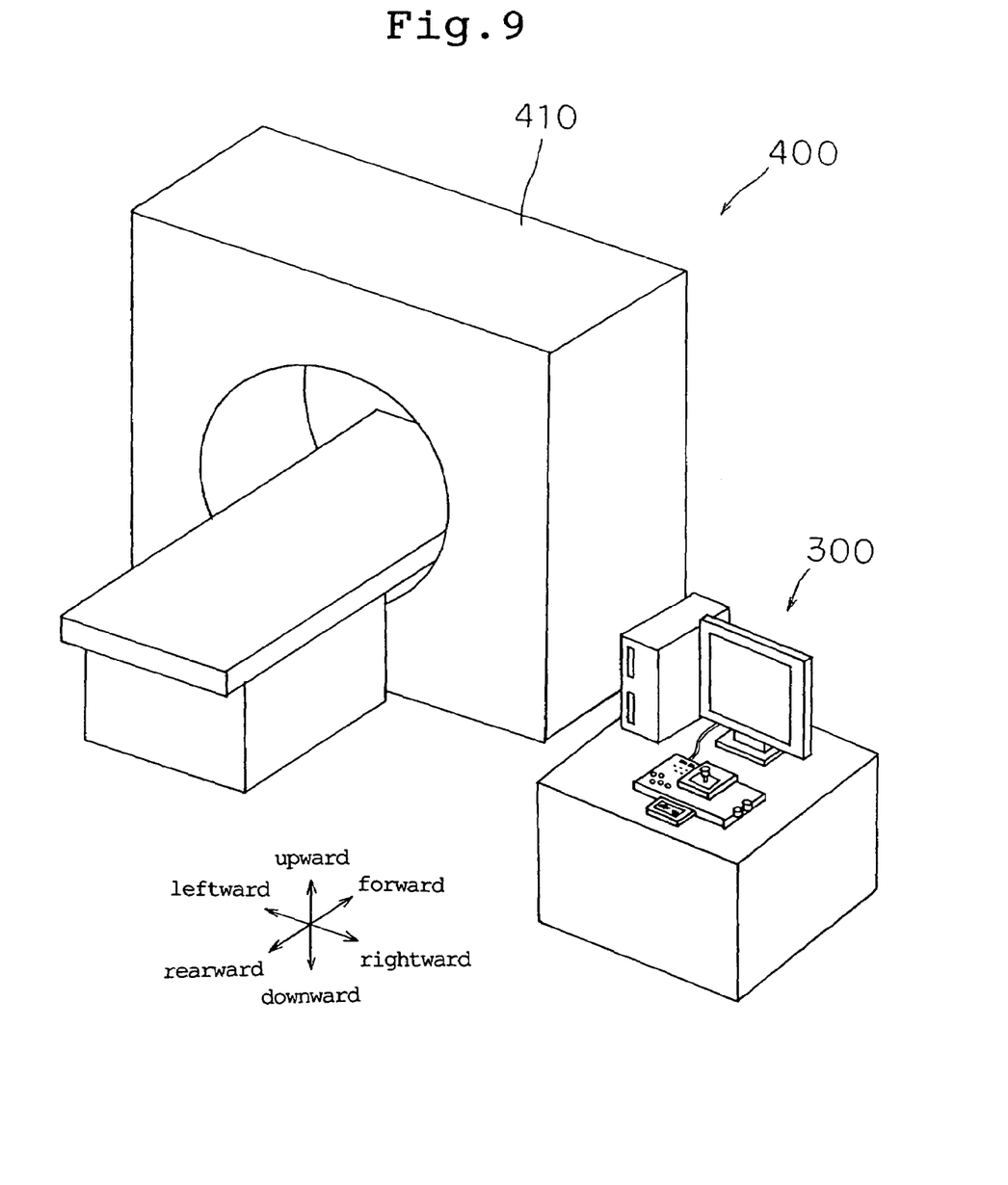
FIG. 9 is a perspective view showing the outer appearance of a tomographic examination system.
Figure 10:
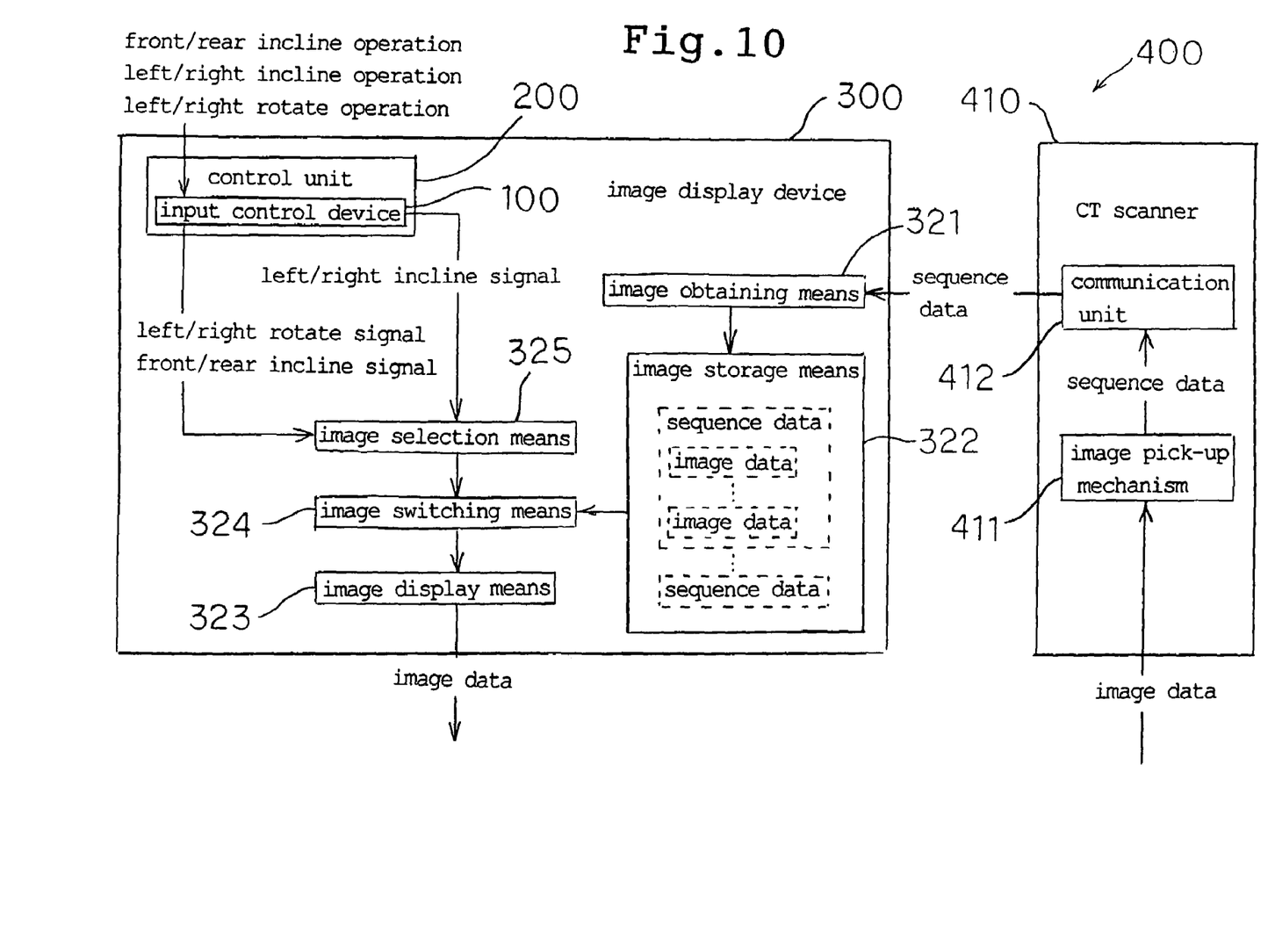
FIG. 10 is a schematic view showing the logical structure of a tomographic examination system.

As shown in FIG. 7 and FIG. 8, control unit 200 of this embodiment is formed as a portion of image display device 300, and is connected to main unit 212 together with display unit 211. As shown in FIG. 9 and FIG. 10, image display device 300 of this embodiment is formed as a part of tomographic examination system 400, and is connected to CT scanner 410.

Image display device 300 of this embodiment includes CPU 301 as the hardware that serves as the main unit of a computer, and this CPU 301 is connected by bus line 302 to hardware such as: ROM 303; RAM 304; HDD (Hard Disk Drive) 305; FDD (FD drive) 307 in which FD (Floppy Disks) 306 are loaded exchangeably; CD drive 309 in which CD (Compact Disk)-ROMs 308 are loaded exchangeably, control unit 200, display unit 211, and I/F unit 311.

CT scanner 410 includes image pick-up mechanism 411, which is a means for picking up an image; and communication unit 412, which is an image supply means; and image pick-up mechanism 411 picks up a plurality of sequence tomographic image data from a human body (not shown in the figure). The plurality of frames of image data that are sequentially picked up from a subject's body are stored as sequence data, and communication unit 412 transmits the data to image display device 300.

In image display device 300 of the present embodiment, hardware such as ROM 303, RAM 304, HDD 305, exchangeable FD 306, and exchangeable CD-ROM 308 correspond to information storage media, and a computer program or resource for CPU 301 is stored in at least one of these components. This software is installed in advance in image display device 300 and then read to CPU 301 at the time of activating image display device 300.

In this way, CPU 301 reads out an appropriate computer program and executes various processing, whereby image display device 300 of the present embodiment logically includes, as various functions, various means, such as image obtaining means 321, image storage means 322, image display means 323, image switching means 324, and image selection means 325, as shown in FIG. 10.

Image obtaining device 321 corresponds to the function by which CPU 301, in accordance with a computer program that is stored in RAM 304, recognizes the received data of I/F unit 311, whereby image obtaining device 321 obtains sequence data from CT scanner 410. Image storage means 322 corresponds to storage areas that are constructed in HDD 305 such that CPU 301 recognizes the areas in accordance with the above-described computer program, and image storage means 322 thus stores sequence data that have been obtained by image obtaining means 321.

Figure 11:
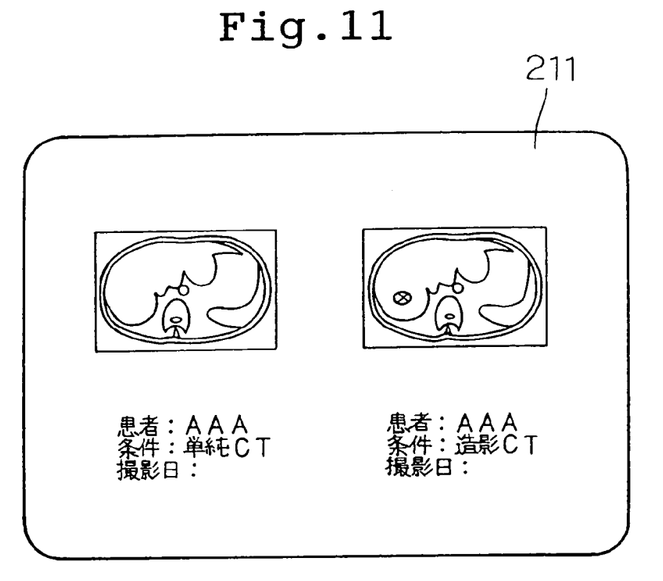
FIG. 11 is a frontal view showing a displayed image of a display unit.

Image display means 323 corresponds to the function by which CPU 301 causes the stored data of HDD 305 to be displayed on display unit 211, whereby at least one frame of image data from the sequence data that are stored in image storage means 322 is displayed. The display may be controlled to various forms, but image display device 300 of the present embodiment takes as its basic form a parallel display to the left and to the right of related frames of image data of two sets of sequence data, as shown in FIG. 11.

Figure 12:
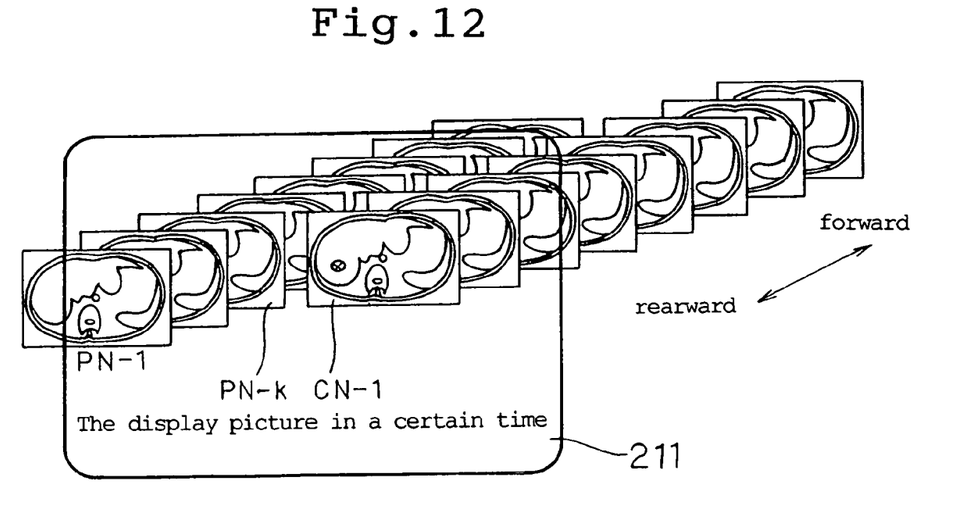
FIG. 12 is a schematic view showing the data structure of sequence data.

The following description corresponds to the function by which CPU 301 recognizes the control signals of control unit 200 and executes prescribed data processing, and image switching means 324 switches image data that are displayed by image display means 323 in accordance with the input control of joystick 203 of control unit 200, as shown in FIG. 12.

More specifically, rotating joystick 203 to the right causes a plurality of frames of image data of the sequence data that are displayed to sequentially switch in the forward direction, and rotating joystick 203 to the left causes sequence switching in the reverse direction. At this time, input control device 100 detects the angle of rotation of control part 102 to both the right and left in three steps, as previously described, and the image data are switched at three levels of speed in accordance with this angle of rotation.

When joystick 203 is forwardly inclined, the plurality of frames of image data of the sequence data that are displayed are switched just one frame in the forward direction, and when joystick 203 is rearwardly inclined, the displayed image data are switched one frame in the reverse direction. Further, when a pair of frames of image data are displayed as previously described, the default setting establishes both frames of image data as objects of processing, and rotation of joystick 203 to the left and right or inclination of joystick 203 in a forward or rearward direction therefore causes the displayed image data of the two sets of sequence data to switch at the same speed without changing synchronization.

When a pair of frames of image data are displayed as previously described, image selection means 325 selects the objects of processing in accordance with inclination to the left and right of joystick 203 of control unit 200. More specifically, when a pair of frames of image data is being displayed as previously described, the default setting establishes both images as the objects of processing, but inclination of joystick 203 to the right in this state causes the selection of only the frame of image data on the right side as the object of processing. Then, rotation of joystick 203 and forward or rearward inclination of joystick 203 in this state causes switching of only the frame of image data on the right without switching of the frame of image data on the left.

Just one inclination of joystick 203 to the left when the frame of image data on the right is selected causes a return to the initial state in which both of the two frames of image data are selected as the objects of processing, and when joystick 203 is again inclined to the left from this initial state, only the frame of image data on the left is selected as the object of processing.

Each of the various means of above-described image display device 300 is realized through the use of hardware such as HDD 305 or I/F unit 311 as necessary, but the major portion of these means is realized through the operation of CPU 301, which is hardware, in accordance with a computer program that has been stored in an information storage medium such as RAM 304.

This type of computer program is stored on an information storage medium such as RAM 304 in the form of software for causing CPU 301 to execute processing such as, for example: a process for receiving sequence data from CT scanner 410 at I/F unit 311; a process for storing the received sequence data on HDD 305; a process for displaying image data of this stored sequence data on display unit 211; a process for sequentially switching this image data that are being displayed in the forward or reverse direction in accordance with the rotation to the left or right of joystick 203 of control unit 200; a process for switching this image data are being displayed one frame at a time in the forward or reverse direction in accordance with forward or backward inclination of joystick 203; and a process for, when a pair of frames of image data are being displayed, selecting the object of processing in accordance with inclination of joystick 203 to the right or left.

The tomographic examination method in tomographic examination system 400 of the present embodiment of the above-described construction is next described in order. A plurality of frames of tomographic image data are first picked up from a patient's body (not shown in the figure) by means of CT scanner 410, and this plurality of frames of image data are registered in image display device 300 as sequence data.

When the sequence data have been registered in image display device 300, the operator (not shown in the figure) executes a prescribed operation in control unit 200 such that frames of the image data of the sequence data are displayed on display unit 211. When data that are picked up from a patient and registered in image display device 300 of the present embodiment include, for example, sequence data in which a contrast medium has been used and sequence data in which a contrast medium has not been used, frames of image data of the two types sequence data for the same tomographic position can be displayed in parallel on the right and left of the display screen, as shown in FIG. 11.

Although the two frames of image data that are displayed in parallel to the right and left as previously explained are switched at the same speed while in synchronization according to the basic operation of image display device 300 of the present embodiment, the two frames of image data can also, as one application of this operation, be set to different switching speeds.

Figure 13:
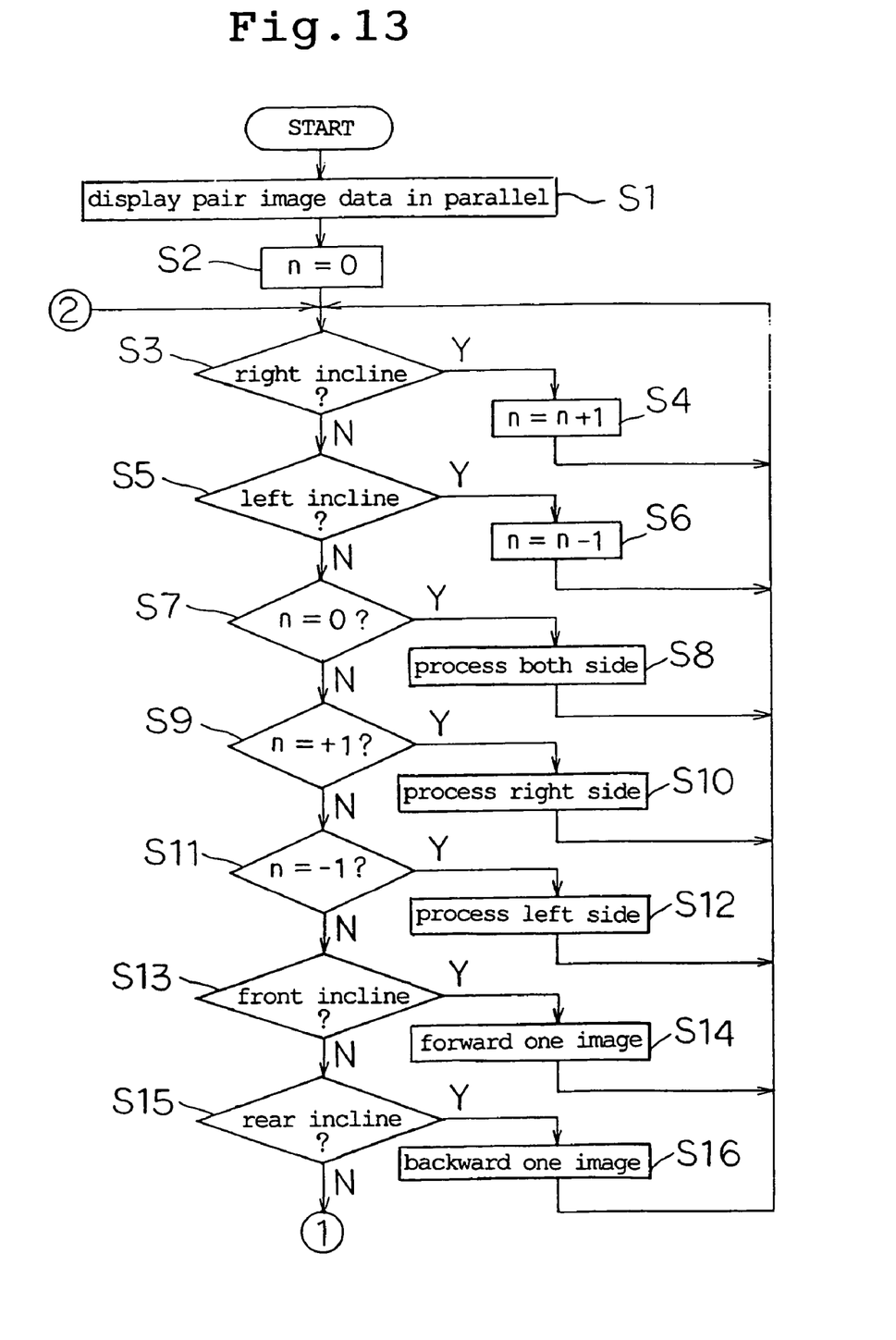
FIG. 13 is a flow chart showing the first half of an image display method by an image display device.

In such a case, as shown in FIG. 13, both of the pair of frames of image data that are displayed in parallel to the right and left are initially set as the objects of processing (Steps S2 and S7–S8), but the object of processing is switched and set to the frame on the left, to the frame on the right, or to both frames each time the operator inclines joystick 203 of control unit 200 to the left or right (Steps S3–S12).

As previously described, when joystick 203 is forwardly inclined while the object of processing has been selected (Step S13), the image data of the object of processing that is displayed is switched just one frame forward (Step S14) as shown in FIG. 12, and when joystick 203 is rearwardly inclined, the image data are switched just one frame to the reverse (Steps S15 and S16).

Figure 14:
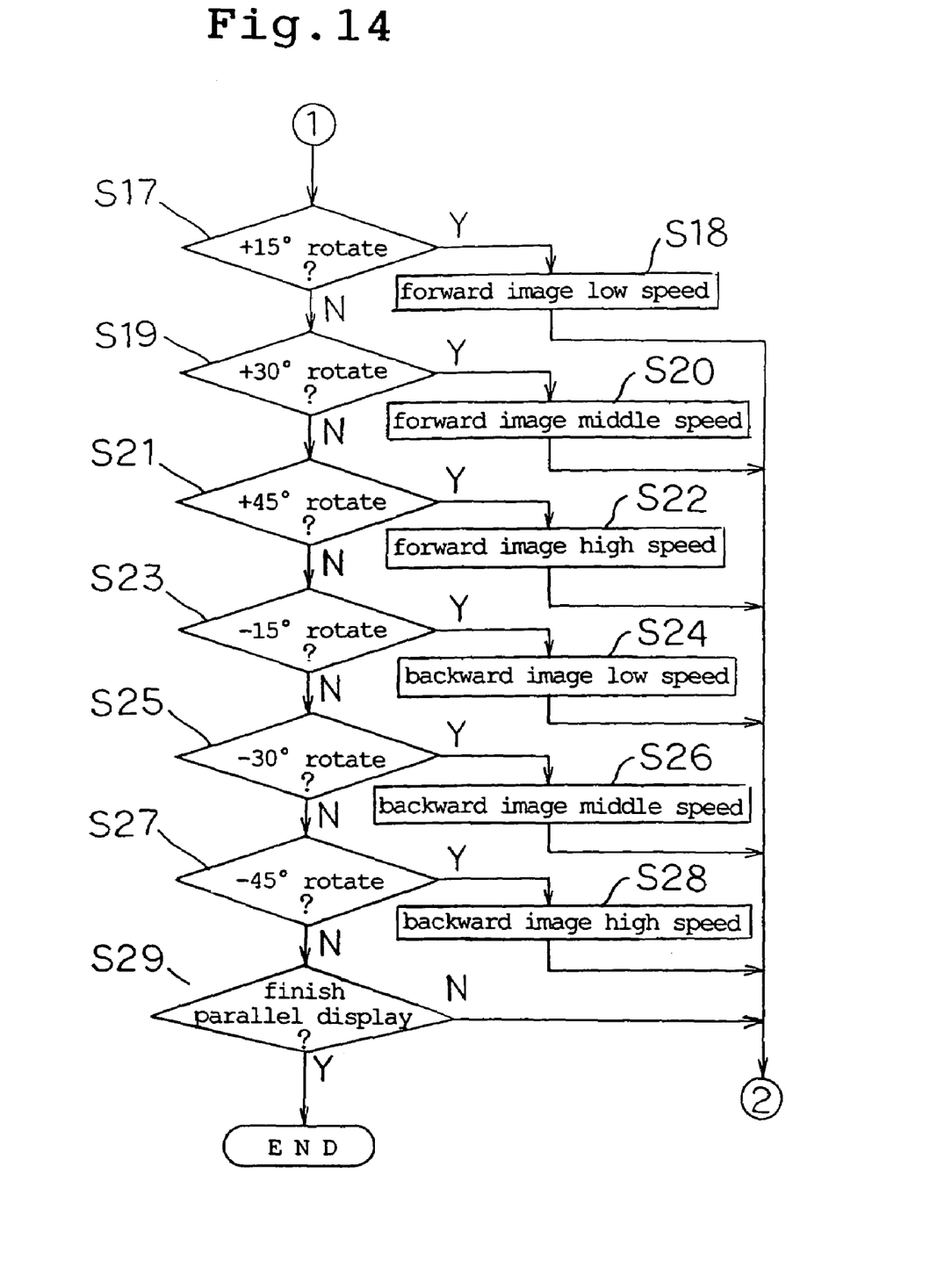
FIG. 14 is a flow chart showing the second half of an image display method by an image display device.

Further, as shown in FIG. 14, when joystick 203 is rotated toward the right, the image data of the object of processing that are being displayed are sequentially switched in the forward direction at high, medium or low speed in accordance with the angle of rotation (Steps S17–S22), and when joystick 203 is rotated toward the left, the image data are switched in the reverse direction at a speed that accords with the angle of rotation (Steps S23–S28).

The pair of frames of image data that are displayed are initially synchronized to the position of pick-up of the patient's body, and when the two frames are made to be the object of processing in this state, the two forms of sequence data are switched in the forward or reverse direction while kept in synchronization.

However, if only one of the pair of sequence data is switched in the forward or reverse direction as the object of processing, the positions in the forward or rearward direction of the patient's body of the displayed pair of frames of image data will diverge.

If, for example, joystick 203 is displaced downward in such a case, the position in the forward or rearward direction of the patient's body of the frame of image data that is not selected can be set in synchronization with the position in the forward or rearward direction of the patient's body of the frame of image data that is selected.

As described hereinabove, image display device 300 of tomographic examination system 400 of the present embodiment can display image data of a plurality of sequence tomographic images that have been picked up from a patient's body by CT scanner 410 on display unit 211, and because these displayed image data can be switched a single frame in the forward or reverse direction by forward or rearward inclination of joystick 203, the image data that an operator wishes to view can be precisely searched.

In addition, rotating joystick 203 to the right and left enables image data that are being displayed to be sequentially switched in the forward or reverse direction, thereby enabling rapid searching of a plurality of frames of sequence image data. In particular, the switching speed can be controlled by the angle of rotation of joystick 203, and a plurality of frames of sequence image data can therefore be searched with ease.

Further, a pair of associated frames of image data can be displayed in parallel on display unit 211, and in such a case the pair of image data can be switched at the same time and in synchronization, thereby enabling easy study and comparison of the two sets of sequence data. Inclining joystick 203 to the right or left enables selection of the image data that is to be the object of processing, thereby enabling free viewing of the image data.

In control unit 200 of the present embodiment, moreover, joystick 203 returns to its initial position automatically upon release of manual operation, and there is consequently no need to manually return joystick 203 to the initial position. Tomographic examination system 400 of the present embodiment therefore enables a plurality of sequence tomographic image data that are picked up from the body of a human body to be viewed by easy control, and further, enables an improvement in the controllability of tomographic examination.

In particular, in tomographic examination system 400 of the present embodiment, the directions of CT scanner 410, display unit 211, and joystick 203 all coincide as shown in FIG. 9, and the operator can therefore effectively recognize the relative orientation of the patient's body, the displayed image, and the input control. In control unit 200 of the present embodiment, moreover, the indication on the upper end of joystick 203 of the directions of forward and backward, right and left inclination as shown in FIG. 3 further improves the controllability of the device.

In input control device 100 of control unit 200 of the present embodiment, moreover, one four-directional switch 101 that is connected to joystick 203 is mounted on first circuit substrate 106 and installed on rotating part 107, and sensor elements 116 are mounted on large-scale second circuit substrate 115 that is installed on base part 108. The means for detecting inclination of joystick 203 to the right and left and inclination forward and rearward as well as for detecting rotation of joystick 203 to the right and left can therefore be realized by marketed package components, and input control device 100 therefore features simple construction and superior productivity.

Although only three sensor elements 116 are mounted on second circuit substrate 115, the angle of rotation of joystick 203 toward both the left and right is detected in three steps by combining the detection results of these three sensor elements 116, whereby excellent functionality is realized by means of a small number of components.

The present invention is not limited to the above-described embodiment and allows a variety of modifications within the scope of the invention. As an example, although a case was presented in which the tomographic images of a patient's body were captured by means of CT scanner 410 in the above-described embodiment, the images may also be obtained by an MRI device (not shown in the figure). In addition, although a case was presented in which the plurality of sequence image data of sequence data were composed of tomographic images of a patient's body in the above-described embodiment, the sequence data may also take the form of, for example, moving picture data.

Figure 15:
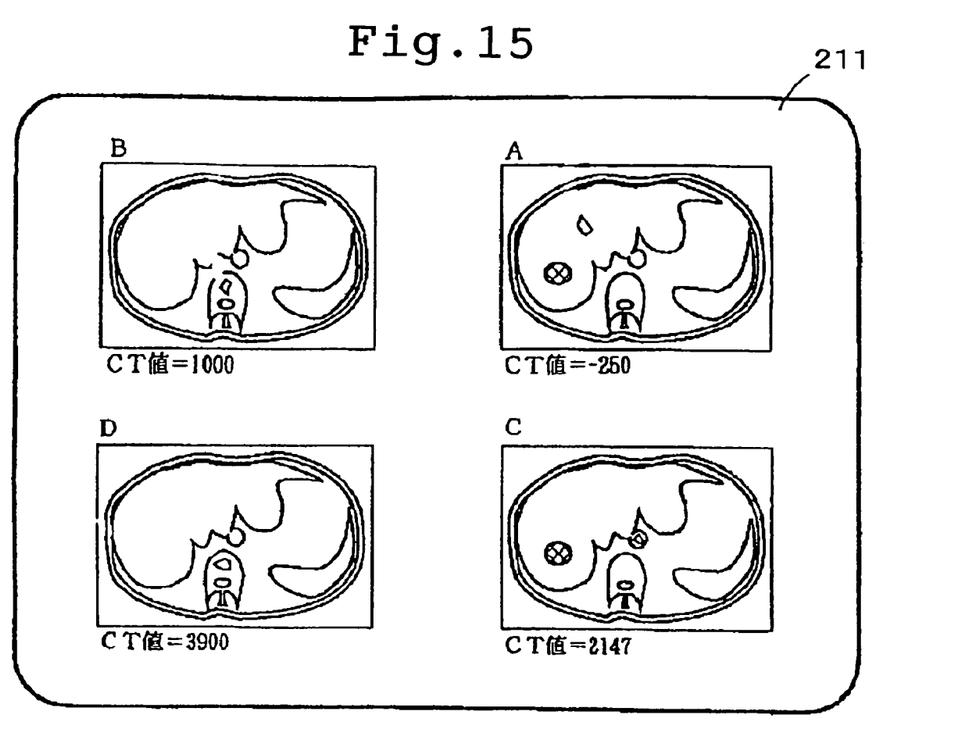
FIG. 15 is a frontal view showing an example of a modification of a displayed image.

Further, although a case was presented in which image display device 300 displayed a pair of frames of image data to the left and right in parallel on display unit 211 in the above-described embodiment, it is obviously also possible for only one frame of the image data to be displayed, or for two or more frames of image data to be displayed, as shown in FIG. 15.

Further, although a case was presented in the above-described embodiment in which image data of two sets of differing sequence data were displayed in parallel, it is also possible, for example, to display a pair of frames of image data of different forward/rearward position in one set of sequence data, or to display a plurality of images of a single frame of image data that has undergone different image processing.

Although a case was presented in the above-described embodiment in which four-directional switch 101 was employed as the multidirectional switch in input control device 100, the multidirectional switch may also be an eight-directional switch, or a multidirectional sensor may be used for analog detection of the angle of inclination.

Although a case was described in which three sensor elements 116 detect the angle of rotation to the left and right in three steps every 15°, the number of these sensor elements 116, the number of detection steps, and the angle of detection may be adjusted as desired, and the angle of rotation may be detected without steps by means of an analog sensor.

Although a case was presented in the above-described embodiment in which: single frame switching of image data in the forward or reverse direction was effected by the forward and rearward inclination of joystick 203, sequence switching of image data in the forward or reverse direction was effected by the rotation of joystick 203 to the left and right, selection of the object of processing was effected by inclination of joystick 203 to the left and right, and the recovery of synchronization of the forward or reverse position of a plurality of frames of image data was effected by downward displacement of joystick 203, the combination of these manual operations and image controls may be variously set according to preference.

Although a case was presented in the above-described embodiment in which, as methods of manipulating joystick 203, inclination to the front and rear, inclination to the right and left, and rotation to the right and left were each executed individually, these operations may also be carried out simultaneously. In such a case, as shown in FIG. 3, the forward, rearward, right and left directions of inclination are indicated on the upper end of joystick 203 in control unit 200 of the present embodiment, and when joystick 203 is rotated, this rotation will not cause the indicated directions of inclination to diverge from the actual directions of inclination, and mishandling of joystick 203 can therefore be effectively prevented.

In addition, the angle of rotation of joystick 203 is limited to 45° for rotation to both the left and the right, and mishandling can therefore be more effectively prevented. Further, although a case was presented in which the angle of rotation of joystick 203 is limited to 45° for rotation to the left and right in the above-described embodiment, this angle of rotation may be increased or decreased, or the angle of rotation may not be limited at all.

Finally, a case was described in the foregoing embodiment in which CPU 301 operates in accordance with a computer program that is stored in, for example, RAM 304, and as a result, various means are logically realized as the various functions of image display device 300. However, each of these various means may also be realized as an individual and characteristic unit of hardware; or a portion may be stored in, for example, RAM 304 as software and a portion may be formed as hardware.

The invention claimed is:

1. An input control device, comprising:
a control part that is manipulated to effect input;
a support mechanism for supporting said control part to allow free inclination in an X-axis direction and a Y-axis direction that are mutually orthogonal;

an inclination recovery means for applying force against the direction of inclination to return said control part to the initial position of said X-axis direction and said Y-axis direction;
an X-axis detection means for detecting inclination of said control part from its initial position in said X-axis direction;
a Y-axis detection means for detecting inclination of said control part from its initial position in said Y-axis direction;
a rotating part on which said support mechanism, said inclination recovery means, said X-axis detection means, and said Y-axis detection means are mounted as a single unit;
an axial support mechanism on which said rotating part is axially supported to allow free rotation around a Z-axis that is orthogonal to said X-axis direction and said Y-axis direction;
a rotation recovery means for applying force against the direction of rotation to return said rotating part to its initial position around the Z-axis; and
sensor elements for detecting rotation of said rotating part from an initial position around the Z-axis, wherein
one multidirectional switch includes at least said control part, said support mechanism, said inclination recovery means, said X-axis detection means, and said Y-axis detection means;
a first circuit substrate, on which this multidirectional switch is mounted, is installed on said rotating part;
said rotating part is axially supported rotatably on a base part by said axial support mechanism;
said sensor elements are mounted on a second circuit substrate that is installed on said base part;
said input control device comprises a detection part secured to said rotating part;
said detection part has at least one notch formed at a position so that said at least one notch confronts said sensor elements in accordance with rotation of said rotating part;
said sensor elements each configured to detect the presence of said at least one notch; and
rotation of said rotating part is detected in a forward and a reverse direction in a plurality of steps by combination of detection results of said at least one notch by said sensor elements.

2. An image display device, comprising:
an input control device according to the description of any one of claim 1;
an image storage means for storing at least one sequence data that are composed of a plurality of sequence frames of image data;
an image display means for displaying at least one frame of said image data from said sequence data that are stored in said image storage means; and
an image switching means for sequentially switching said image data that are displayed on said image display means in a forward or reverse direction in accordance with rotation of a control part of said input control device in a forward or reverse direction around a Z-axis.

3. An image display device according to claim 2, wherein said image switching means switches said image data that are displayed on said image display means one frame at a time in the forward or reverse direction with each inclination in the forward or reverse direction of the Y-axis of the control part of said input control device.

4. An image display device according to claim 2, wherein said image display means displays a plurality of frames of said image data in parallel and said image switching means switches a plurality of frames of said image data that are being displayed in parallel on said image display means at the same speed while keeping the plurality of frames of said image data synchronized.

5. An image display device according to claim 4, further comprising image selection means for selecting the object of processing of said image switching means from a plurality of frames of said image data that are being displayed in parallel on said image display means in accordance with inclination in the X-axis direction of the control part of said input control device.

6. An image display device according to claim 2, wherein said image switching means switches said image data that are displayed on said image display means at a speed that accords with the angle of rotation of the control part of said input control device.

* * * * *